US008532771B2

United States Patent
Daum et al.

(10) Patent No.: US 8,532,771 B2
(45) Date of Patent: Sep. 10, 2013

(54) MAXIMUM PACING RATE LIMITER SYSTEM

(75) Inventors: Douglas R. Daum, Woodbury, MN (US); Geng Zhang, Newbury Park, CA (US); Qingsheng Zhu, Wexford, PA (US); Gerrard M. Carlson, Champlin, MN (US); Julio C. Spinelli, Lakewood Ranch, FL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 294 days.

(21) Appl. No.: 13/115,825

(22) Filed: May 25, 2011

(65) Prior Publication Data

US 2011/0230926 A1   Sep. 22, 2011

Related U.S. Application Data

(62) Division of application No. 11/225,712, filed on Sep. 13, 2005, now Pat. No. 7,953,486, which is a division of application No. 10/053,223, filed on Jan. 17, 2002, now Pat. No. 6,963,778.

(51) Int. Cl.
*A61N 1/365* (2006.01)

(52) U.S. Cl.
USPC .............. 607/18; 607/19; 607/20; 607/25

(58) Field of Classification Search
USPC .................................. 607/9, 18–25
See application file for complete search history.

(56) References Cited

U.S. PATENT DOCUMENTS

| 4,378,020 | A | 3/1983 | Nappholz et al. |
|---|---|---|---|
| 4,527,568 | A | 7/1985 | Rickards |
| 5,086,774 | A | 2/1992 | Duncan |
| 5,713,930 | A | 2/1998 | van der Veen et al. |
| 5,941,903 | A | 8/1999 | Zhu et al. |
| 6,067,472 | A | 5/2000 | Vonk et al. |
| 6,161,042 | A | 12/2000 | Hartley et al. |
| 6,711,438 | B1 | 3/2004 | McClure et al. |
| 6,721,599 | B2 | 4/2004 | de Vries |
| 6,836,682 | B2 | 12/2004 | Van Dam |
| 7,953,486 | B2 | 5/2011 | Daum et al. |
| 2006/0009812 | A1 | 1/2006 | Daum et al. |

OTHER PUBLICATIONS

"U.S. Appl. No. 10/053,223, Notice of Allowance mailed May 20, 2005", 6 pgs.
"U.S. Appl. No. 10/053,223, Response filed Feb. 7, 2005 to Restriction Requirement mailed Jan. 12, 2005", 2 pgs.
"U.S. Appl. No. 10/053,223, Response filed Oct. 19, 2004 to Restriction Requirement mailed Sep. 20, 2004", 2 pgs.

(Continued)

*Primary Examiner* — Mark W Bockelman
(74) *Attorney, Agent, or Firm* — Schwegman Lundberg & Woessner, P.A.

(57) ABSTRACT

A maximum pacing rate limiter for use in adaptive rate pacing in conjunction with a cardiac rhythm management system for a heart. The maximum pacing rate limiter may function to measure an interval, termed the ERT interval, between a paced ventricular evoked response and a T-wave. The maximum pacing rate limiter may further function to maintain the ERT interval at less than a certain percentage of the total cardiac cycle. In one disclosed embodiment, a maximum pacing rate limiter calculates an ERT rate based on the detected paced ventricular evoked response and the T-wave, and the pacing rate limiter module further communicates the minimum of the ERT rate and an adaptive-rate sensor indicated rate to a pacemaker.

20 Claims, 5 Drawing Sheets

(56) References Cited

OTHER PUBLICATIONS

"U.S. Appl. No. 10/053,223, Restriction Requirement mailed Jan. 12, 2005", 5 pgs.

"U.S. Appl. No. 10/053,223, Restriction Requirement mailed Sep. 20, 2004", 5 pgs.

"U.S. Appl. No. 11/225,712 Non-Final Office Action mailed Aug. 6, 2010", 5 pgs.

"U.S. Appl. No. 11/225,712, Non-Final Office Action mailed Dec. 18, 2009", 8 pgs.

"U.S. Appl. No. 11/225,712, Notice of Allowability mailed Jan. 24, 2011", 4 pgs.

"U.S. Appl. No. 11/225,712, Response filed May 13, 2010 to Non Final Office Action mailed Dec. 18, 2009", 7 pgs.

"U.S. Appl. No. 11/225,712, Response filed Nov. 8, 2010 to Non Final Office Action mailed Aug. 6, 2010", 7 pgs.

"U.S. Appl. No. 11/225,712, Restriction Requirement mailed Jul. 22, 2009", 9 pgs.

"U.S. Appl. No. 12/225,712, Response to Restriction Requirement, filed Sep. 22, 2009", 7 pgs.

MAXIMUM PACING RATE LIMITER SYSTEM

RELATED APPLICATIONS

The present application is a divisional of U.S. patent application Ser. No. 11/225,712 filed on Sep. 13, 2005 and entitled "Maximum Pacing Rate Limiter Implemented Using the Evoked Response—T-Wave Interval, which is a divisional of U.S. patent application Ser. No. 10/053,223 filed on Jan. 17, 2002 and entitled "Maximum Pacing Rate Limiter Implemented Using the Evoked Response—T-Wave Interval," now issued as U.S. Pat. No. 6,963,778, the entirety of which are hereby incorporated by reference.

TECHNICAL FIELD

This invention relates to cardiac rhythm management systems for the heart. In addition, the invention relates to a maximum pacing rate limiter implemented using the evoked response—T-wave interval.

BACKGROUND

Cardiac rhythm management (CRM) systems are a common solution for problems associated with the heart's inherent pacing capabilities. The fundamental components of a CRM system may include a pacemaker for creating electrical pulses to stimulate the heart and one or more electrodes for delivering the electrical pulses and sensing the heart's contraction in reaction to the stimulus. The heart's contraction in response to the electrical pulse is termed the evoked response.

Typically, the CRM system may monitor the heart for a set escape interval. An escape interval is a period of time during which the pacemaker will wait to send another electrical pulse to the heart. If this escape interval is exhausted without detection of a natural heart contraction, an electrical pulse may be delivered to the heart. Electrical pulses may be delivered at a set pacing stimulation frequency based on the duration of the escape interval.

Pacing abnormalities may occur in both the atrial and ventricular portions of the heart. For heart abnormalities, including such examples as total or partial heart block, arrhythmias, myocardial infarctions, congestive heart failure, congenital heart disorders, and various other problems, a pacing system for the ventricles may include one or more adaptive rate sensors. An adaptive rate sensor is a sensor that may function to monitor an individual's physical activity. If the adaptive rate sensor determines that additional cardiac output is desirable for the physiological requirements of an activity, the adaptive rate sensor may increase an adaptive-rate sensor indicated rate. The adaptive-rate sensor indicated rate is a rate provided by an adaptive rate sensor that may be used to decrease the duration of the escape interval of a pacemaker so that pacing stimulation frequency increases. As the pacing stimulation frequency is increased and the escape interval decreased, the heart is caused to beat at an increased rate and cardiac output may thereby be increased.

A prior art CRM system 100, including an adaptive rate sensor 110 coupled to a CRM device 130, is shown in FIG. 1. The adaptive rate sensor 110 may include an adaptive rate sensor or other such device or signal that functions to provide an adaptive-rate sensor indicated rate. The adaptive rate sensor 110 may communicate the adaptive-rate sensor indicated rate to the CRM device 130. The CRM device 130 may be a pacemaker or other such device that functions to pace the heart. The CRM device 130 may calculate an escape interval based on the adaptive-rate sensor indicated rate and deliver electrical pulses to the heart based on the escape interval.

Adaptive rate sensors may be used to detect a wide range of cardiac-output requirements and increase the pacing stimulation frequency according to the increased activity of the individual. Examples of activities that may necessitate an increase in pacing stimulation frequency are strenuous activities such as jogging or swimming, although any increase in activity may heighten an individual's cardiac output needs.

Presently there are three major types of commercial adaptive rate sensors available, including activity sensors, minute ventilation sensors, and QT interval sensors. All three types of sensors use different physiological criteria to measure changes in activity and therefore increased need for cardiac output. Unfortunately, all three sensor types may exhibit limitations in their use under various circumstances.

An activity sensor measures the acceleration of an individual by typically using an accelerometer. In situations such as, for example, when an individual goes from standing still to walking, the individual's need for cardiac output increases. The activity sensor measures an increase in acceleration as the individual walks and therefore increases the pacing stimulation frequency for the heart. This increase in the frequency of stimulation increases cardiac output. A limitation of this type of sensor is that the increase in pacing stimulation frequency is not always proportional to the increased workload for the individual, such as when the individual remains relatively stationary (and therefore the sensor records no change in acceleration) but experiences a heightened increase in the need for cardiac output. Examples of this situation include riding a stationary bike, where no acceleration occurs, and to a lesser extent, walking up stairs, where workload is not proportional to acceleration.

A minute ventilation sensor functions to monitor the breathing of the individual and equates increased respiration with the need for increased cardiac output. Specifically, the minute ventilation sensor can measure the volume of air inhaled and exhaled during a particular period of time, typically by measuring transthoracic impedance. An example of such a minute ventilation device can be found in U.S. Pat. No. 6,161,042 to Hartley et al. If the impedance-based minute ventilation sensor detects an increase in respiration, it assumes that there is an increase in the need for cardiac output and the sensor therefore increases the pacing stimulation frequency. While this type of sensor functions more proportionally to workload, a limitation of this sensor is the significant variation among individuals requiring individualized calibration. Another limitation of the minute ventilation sensor includes motion artifact, a phenomenon wherein certain movements by an individual, such as waving the individual's arms in the air, may be incorrectly interpreted by the impedance-based sensor as an increase in respiration.

A QT interval sensor functions to measure the interval between stimulus of the ventricle (Q) and the appearance of the T-wave signifying repolarization of the ventricle, as indicated on a typical electrocardiogram. A shortening of the QT interval may represent an increase in the need for cardiac output. Once again, a limitation of this type of sensor is a variation in QT intervals from individual to individual. For example, some individuals exhibit a QT interval that actually lengthens in duration during situations in which increased cardiac output is desirable. In addition, the QT interval sensor detects the interval from stimulation of the ventricle Q to detection of the T-wave, but contraction of the ventricle muscle actually occurs approximately 50 ms after stimulus. Therefore, in the relatively small QT interval of 120-250 ms, this lag between stimulus and contraction can have a significant impact on the accuracy of the measured rate of contraction.

A shortcoming common to all adaptive rate sensors is the failure to provide meaningful limitation on pacing stimulation frequency at high pacing rates. This failure to limit the pacing rate can lead to situations in which the pacing stimulation frequency exceeds the cardiac output needs of the individual. More importantly, the increase of pacing stimulation frequency beyond a certain threshold can actually result in a decrease, rather than increase, in cardiac output. This phenomenon may occur because the ventricle may be caused to contract at a rate that is faster than the ventricle can fill with blood.

Regarding activity sensors, because the rate provided by an activity sensor is not proportional to workload, there is no feedback provided to allow the activity sensor to immediately determine if the activity-sensor indicated rate exceeds the needs of the individual. Therefore, because no negative feedback exists, it is possible at high pacing stimulation frequencies for the activity sensor to provide adaptive-rate sensor indicated rates that exceed the individual's cardiac output needs.

A minute ventilation sensor may be proportional to workload and may exhibit some negative feedback characteristics. However, if a minute ventilation sensor is not calibrated appropriately, it too can indicate rates that exceed the needs of the individual, particularly if motion artifact is introduced. Further, motion artifact limitations are still presented in the minute ventilation sensor.

QT interval sensors do not have negative feedback in their normal operating range for adaptive-rate pacing. In fact, a QT interval sensor demonstrates a positive feedback characteristic because of the methodology utilized by the QT interval sensor to measure increased cardiac output need. This positive feedback is illustrated as follows:
  (a) the QT interval sensor detects a decrease in the duration of the individual's QT interval and therefore increases the adaptive-rate sensor indicated rate;
  (b) the increased adaptive-rate sensor indicated rate causes the pacemaker to decrease the duration of the escape interval, thereby causing an increase in the pacing stimulation frequency;
  (c) the increase in pacing stimulation frequency causes the duration of the individual's QT interval to decrease; and
  (d) the QT sensor detects this additional decrease in the duration of the individual's QT interval and therefore further increases the adaptive-rate sensor indicated rate.

Therefore, positive feedback may occur in this situation where an increase in pacing stimulation frequency can cause a decrease in the duration of an individual's QT interval, thereby causing the QT interval sensor to further increase the adaptive-rate sensor indicated rate.

The most sophisticated CRM systems implement a pair of the adaptive rate sensors described above (commonly activity and either minute ventilation or QT interval) to emphasize the strengths of particular sensors and lessen the limitations associated with each particular individual sensor. Such a system is the PULSAR™ MAX CRM system manufactured by Guidant Corporation, which utilizes an activity sensor in conjunction with a minute ventilation sensor. However, even in combination, the current adaptive rate sensors may have limitations, and therefore the potential exists for increased pacing stimulation frequencies that exceed an individual's cardiac output needs and may actually result in decreased cardiac output.

The adaptive-rate sensor indicated rate is defined herein to further include an intrinsic atrial rate as measured from the atria of the heart. An intrinsic atrial rate is typically utilized as a method of pacing the heart in individuals where natural conduction pathways between the atria and ventricles have been damaged, such as in left branch bundle block. In cases such as these, an electrode or other such sensor is placed in the atria to detect atrial contraction and communicate this contraction to the ventricles via a pacemaker or other device.

A common problem that may occur with use of intrinsic atrial pacing is atrial tachycardia, in which an individual's intrinsic atrial pacing rate reaches irregularly high rates. If the intrinsic atrial rate exceeds a certain threshold, use of the intrinsic atrial rate to pace the ventricles can cause the ventricles to contract at excessive rates. Therefore, use of the intrinsic atrial rate as a method of pacing the ventricles may also result in pacing stimulation frequencies that exceed an individual's cardiac output needs and may actually result in decreased cardiac output.

SUMMARY

Generally, the present invention relates to cardiac rhythm management systems for the heart, and more particularly, to a maximum pacing rate limiter implemented using the evoked response—T-wave interval. In one aspect of the disclosure, a method for limiting a paced heart rate can comprise measuring an ERT interval, the ERT interval spanning detection of a paced ventricular evoked response and detection of a T-wave; calculating a maximum pacing rate based on the ERT interval; and adjusting the paced heart rate based on the maximum pacing rate.

In another aspect of the disclosure, a pacing rate limiter for limiting a paced heart rate may comprise an ER sensor adapted to detect a paced ventricular evoked response and a T sensor adapted to detect a T-wave, wherein the pacing rate limiter calculates an ERT rate based on the paced ventricular evoked response and the T-wave.

In yet another aspect of the disclosure, a cardiac rhythm management system for a heart may comprise a pacemaker module coupled to the heart so as to provide a paced heart rate; a pacing rate limiter module coupled to the pacemaker module; a paced ventricular evoked response sensor module coupled to the pacing rate limiter module, wherein the paced ventricular evoked response sensor module is adapted to detect a paced ventricular evoked response; a T sensor module coupled to the pacing rate limiter module, wherein the T sensor module is adapted to detect a T-wave; and an adaptive rate sensor module coupled to the pacing rate limiter module, wherein the adaptive rate sensor module communicates an adaptive-rate sensor indicated rate to the pacing rate limiter module. The pacing rate limiter module calculates an ERT rate based on the detected paced ventricular evoked response and the T-wave, and the pacing rate limiter module further communicates the minimum of the ERT rate and the adaptive-rate sensor indicated rate to the pacemaker module.

In yet another aspect of the disclosure, a pacing rate limiter for limiting a paced heart rate may comprise a means for detecting a paced ventricular evoked response; a means for detecting a T-wave; and a means for calculating a maximum pacing rate based on the paced ventricular evoked response and the T-wave.

In another aspect of the disclosure, a method for calculating a maximum pacing rate may comprise measuring a cardiac cycle, wherein the cardiac cycle comprises a ventricular relaxation portion and a ventricular contraction portion and limiting the maximum pacing rate to cause the ventricular relaxation portion to be a percentage of the cardiac cycle.

The above summary of the present invention is not intended to describe each disclosed embodiment or every implementation of the present invention. The figures and the detailed description which follow more particularly exemplify these embodiments.

DESCRIPTION OF THE DRAWINGS

The invention may be more completely understood in consideration of the following detailed description of various embodiments of the invention in connection with the accompanying drawings, in which.

Figure 1:
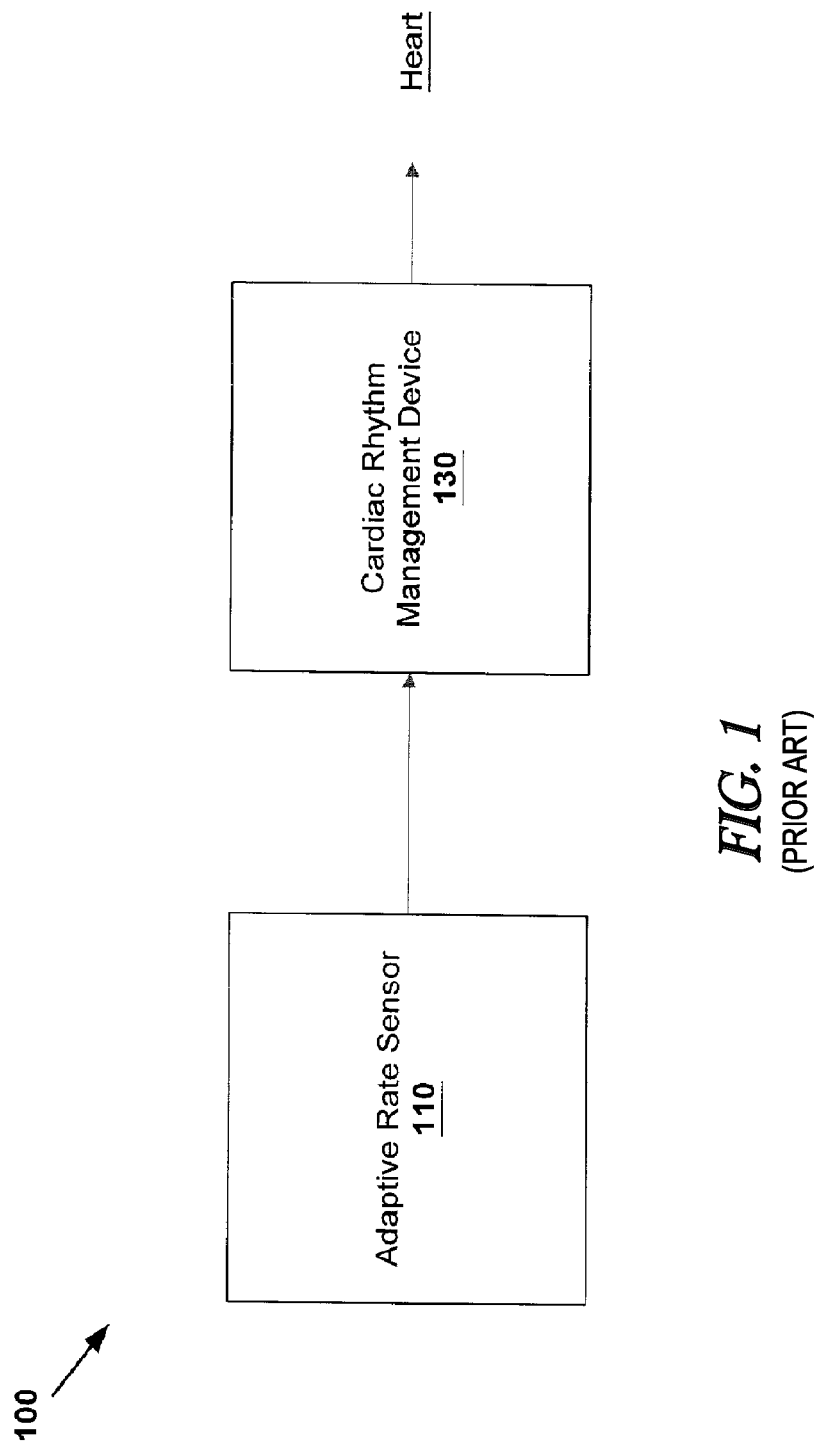
FIG. 1 illustrates a prior art cardiac rhythm management system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to cardiac rhythm management (CRM) systems for the heart. In particular, the present invention is directed to a maximum pacing rate limiter implemented using the evoked response—T-wave interval. While the present invention is not so limited, an appreciation of various aspects of the invention will be gained through a discussion of the examples provided below.

In a typical CRM system, a pacemaker that is coupled to the heart is controlled using one or more adaptive rate sensors. As described above, an adaptive rate sensor functions to monitor the activity of an individual and increase pacing stimulation frequency when physiological needs of the individual require increased cardiac output. Examples of different adaptive rate sensors, as described above, include activity, minute ventilation, and QT interval adaptive rate sensors. An adaptive rate sensor may function to communicate an adaptive-rate sensor indicated rate to a pacemaker. The adaptive-rate sensor indicated rate is a rate provided by an adaptive rate sensor that may be used to adjust the escape interval of a pacemaker so that pacing stimulation frequency increases. The adaptive-rate sensor indicated rate is herein defined to also include an intrinsic atrial rate as measured for individuals suffering from abnormalities such as left bundle branch block or other similar problems. Typically, the pacemaker may increase the pacing stimulation frequency based on the adaptive-rate sensor indicated rate.

A pacing rate limiter according to a preferred embodiment of the present invention may act as an upper limit, or governor, to the adaptive-rate sensor indicated rate. A pacing rate limiter according to a preferred embodiment of the present invention may provide negative feedback, thereby assuring that the pacing stimulation frequency does not exceed the needs of an individual or result in decrease in a cardiac output because of excessive pacing stimulation frequencies.

Figure 2A:
FIG. 2A is an electrocardiogram waveform of a typical heart.
Figure 2B:
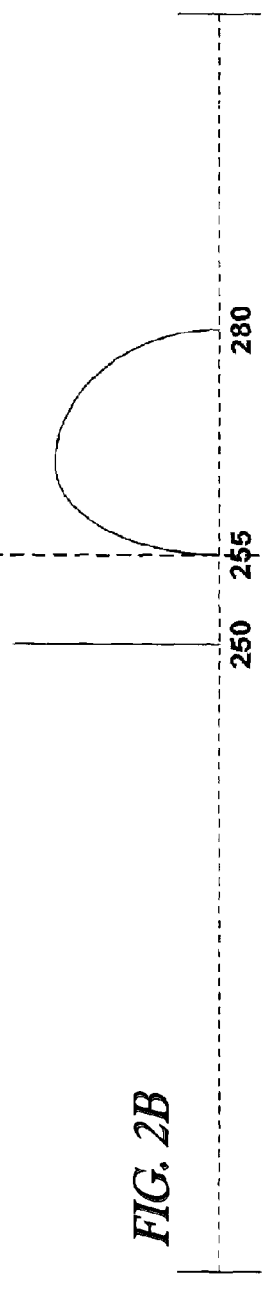
FIG. 2B is a waveform of a typical heart as measured internally using an intra-cardial or subcutaneous electrode.
Figure 2C:
FIG. 2C is a timeline illustrating relaxation and contraction for the ventricles of a typical heart.

The methodology or manner by which a pacing rate limiter according to a preferred embodiment of the present invention may function requires an examination of the physiology of the heart. FIGS. 2A-2C are provided according to an identical scale on an X-axis, the X-axis representing an interval of time. The onset of the interval is marked as 201 and the conclusion is marked as 299. The interval 201-299 may function to represent a single cardiac cycle for a heart.

In FIG. 2A, a typical electrocardiogram (ECG) waveform is provided. As in other ECGs, P represents atrial depolarization, the QRS complex represents ventricular depolarization, and the T-waveform represents ventricular repolarization.

The waveforms as shown in FIG. 2B illustrate measurements taken of a typical heart as measured internally using an intra-cardial or subcutaneous electrode. An electrical pulse 250 is communicated to the heart by a pacemaker or other such device in order to initiate contraction of the ventricles, and waveform ER represents the paced ventricle evoked response, with onset at 255 and conclusion at 280. The ER waveform is the actual response by the ventricular muscle to the electrical pulse 250. The interval between the electrical pulse 250 and the onset of the evoked response 255 is typically approximately 50 milliseconds. This interval 250-255 represents the delay between stimulation of the ventricle and actual onset of contraction of the ventricle. Methods to detect the paced ventricular evoked response, such as through use of small coupling capacitor technology, are now known and are discussed generally in U.S. Pat. No. 5,941,903 to Zhu et al. and U.S. Pat. No. 6,067,472 to Vonk et al., both of which are incorporated herein by reference.

In FIG. 2C, the interval 201-299 on the X-axis once again represents a single cardiac cycle, and intervals R and C represent relaxation and contraction of the ventricles, respectively. During interval R, the ventricles are in a relaxed state, and blood is allowed to fill the ventricles. During interval C, the ventricles are contracting or contracted, and blood is forced from the ventricles.

As FIGS. 2A-2C are all drawn to approximately the same scale on the X-axis, it can be seen that the interval of contraction of the ventricles C can be approximated by the interval QT in FIG. 2A. However, the interval QT fails to account for the lag between the electrical pulse 250 by which the ventricle is stimulated and actual onset of contraction of the ventricles 255.

Therefore, a better approximation of the interval of contraction is shown in FIG. 2B as the interval from the paced ventricular evoked response ER to the T-waveform as shown in FIG. 2A. This interval between the evoked response ER and the T-waveform is herein defined as the ERT interval. Specifically, the ERT interval is the interval between detection of a specified segment of the waveform representing the evoked response ER and detection of a specified segment of the T-waveform. Detection of a specified segment of the evoked response ER and T-waveforms may include onset detection, peak detection, conclusion detection, or may include detection of a different segment of the relevant waveform.

The ERT interval may provide a more precise approximation of the interval C representing the contraction of the ventricles. Measuring two or more ERT intervals and averaging the intervals using known methods, such as for example ensemble averaging, may further refine accurate measurement of the ERT interval.

During typical periods of low activity, the interval R represents approximately 65-75% of the cardiac cycle 201-299 and interval C represents approximately 25-35% of the cardiac cycle. During periods involving increased cardiac output, the contraction interval C decreases in duration as the heart speeds up such that its percentage of the cardiac cycle remains relatively constant. In other words, although the total cardiac cycle, represented by the interval between 201 and 299, may decrease in duration as the pacing stimulation frequency increases and the heart beats faster, the relative percentages that R and C occupy in the cardiac cycle remain relatively constant, or approximately 65-75% and 25-35%, respectively.

Eventually, however, the pacing stimulation frequency reaches a limit such that further increase in stimulation frequency can increase heart rate but the speed of ventricular contraction cannot be further increased. Thus, the contraction interval C becomes a larger proportion of the total cardiac cycle 201-299. This necessarily means that the relaxation interval R becomes a smaller proportion of the total cardiac cycle. Because of this phenomenon, there is less of the cardiac cycle devoted to diastolic filling of the ventricles as represented by R. As the rate of the stimulation frequency further increases, the ventricles have less and less time during relaxation interval R to fill with blood, and at a critical point cardiac output may actually decrease because too much of the total cardiac cycle 201-299 is devoted to contraction without enough time being devoted to relaxation to allow for filling of the ventricles.

It is therefore desirable to ensure that the pacing stimulation frequency is not increased to the point that the contraction interval C occupies too much of the cardiac cycle. As an accurate approximation of interval C, the ERT interval can be measured and compared to the total cardiac cycle to determine the relative percentage of the cardiac cycle devoted to contraction. It is desirable, therefore, to limit the ERT interval as shown in Equation 1:

$$ERT\ \text{interval} < Y\%\ (\text{cardiac cycle}) \qquad (1)$$

In Equation 1, the ERT interval is maintained as no greater than a percentage "Y" of the cardiac cycle.

If the ERT interval is longer than a given percentage "Y" of the cardiac cycle, the pacing stimulation frequency can be limited or decreased. In a preferred embodiment of the invention, the percentage Y is 50%, such that the ERT interval is limited so as never to be greater than 50% of the total cardiac cycle. Other percentages for Y may also be selected. For example, the percentage Y may vary as between approximately 30-60% so as to maximize hemodynamic efficiency. In this manner, the pacing stimulation frequency may be limited such that it never reaches the critical point at which the contraction interval C occupies too great a percentage of the cardiac cycle and therefore cardiac output may be decreased.

In the situation where an artificial stimulus such as a pacemaker is used to pace the heart, an escape interval represents the outer bounds for the length of the cardiac cycle. The escape interval is the period of time that a pacemaker will wait before sending an electrical pulse to the heart. If the pacemaker does not detect a contraction before the conclusion of the escape interval, the pacemaker will send an electrical pulse to the heart. As the escape interval decreases, the pacing stimulation frequency necessarily increases. If the ERT interval occupies more than a certain percentage of the escape interval, because the escape interval is too short in duration (and the pacing stimulation too fast), a decrease in cardiac output may result. Therefore, it would be desirable to maintain the ERT interval at some percentage of the escape interval as shown in Equation 2:

$$\text{escape interval} > k \times (ERT\ \text{interval}) \qquad (2)$$

As this Equation 2 illustrates, the ERT interval, as an approximation of the time the ventricles are contracting, may preferably be maintained as a factor k less than the escape interval. The constant k may be linear or nonlinear, and in a preferred embodiment of the invention may be in the range of 1.8-2.2. The constant k may also vary depending on such factors as how the evoked response ER and T-wave are measured or may vary depending on the particular needs of the individual. If the constant k is set equal to 2, then Equation 2 is identical mathematically to Equation 1 because the ERT interval is maintained at no greater than 50% of the cardiac cycle, or in this case the escape interval.

Figure 3:
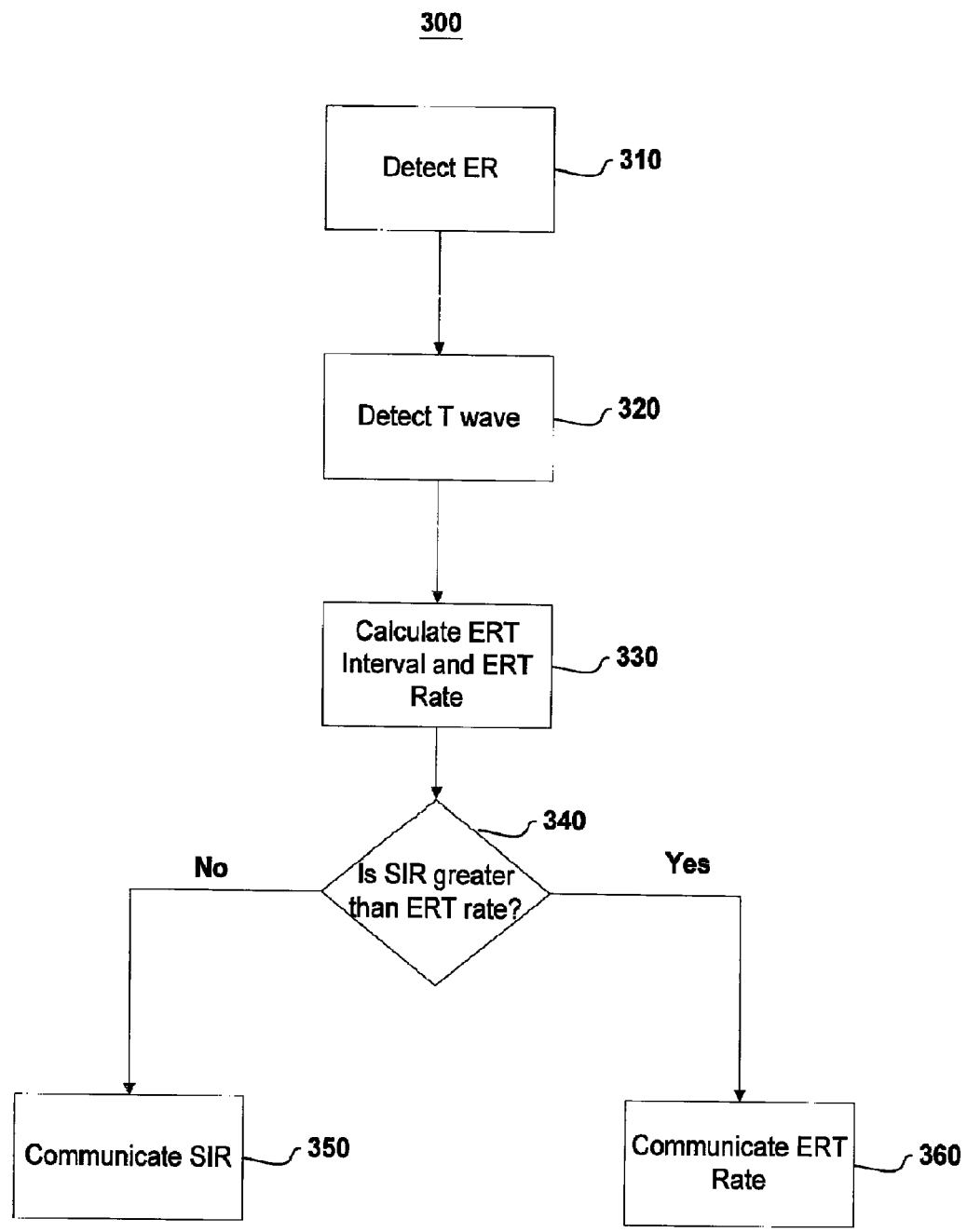
FIG. 3 shows the operational flow of a pacing rate limiter according to an embodiment of the present invention.

Application of the above principles may be employed by a pacing rate limiter according to a preferred embodiment of the invention as illustrated by the methodology 300 shown in FIG. 3. In module 310, a pacing rate limiter detects the paced ventricular evoked response (ER). In module 320, the pacing rate limiter detects the T-wave. The detection in modules 310 and 320 may include detection of the onset, peak, conclusion, or other segment of the waveform depending on the detection method used. In module 330, an ERT interval is calculated as the interval of time between the ER and T-wave. Module 330 further calculates an ERT rate (in seconds) based on the ERT interval as follows in Equation 3:

$$ERT\ \text{rate} = \frac{60}{(k \times ERT\ \text{interval})} \qquad (3)$$

The ERT rate is calculated in Equation 3 by dividing 60 seconds by the product of the constant k, as described in Equation 2, and the ERT interval (measured in seconds). The ERT rate represents the rate of ERT intervals per minute.

Decision module 340 compares an adaptive-rate sensor indicated rate (SIR) provided by an adaptive rate sensor and the calculated ERT rate. Decision module 340 then selects a maximum pacing rate (MPR) as shown in Equation 4:

$$MPR = \text{minimum}(SIR, ERT\ \text{rate}) \qquad (4)$$

As Equation 4 indicates, the MPR will be determined by comparing the SIR and ERT rate and selecting the minimum, or slower, of the two.

If the adaptive-rate sensor indicated rate (SIR) is slower than the ERT rate, the SIR will be communicated to the pacemaker, as shown in module 350. Otherwise, if the ERT rate is slower than the SIR, the ERT rate will be communicated to the pacemaker, as shown in module 360. Therefore, through utilization of this methodology 300, a pacing rate limiter may effectively limit the maximum pacing rate presented to a pacemaker by comparing the SIR to the ERT rate and selecting the ERT rate if the SIR exceeds the ERT rate.

Figure 4:
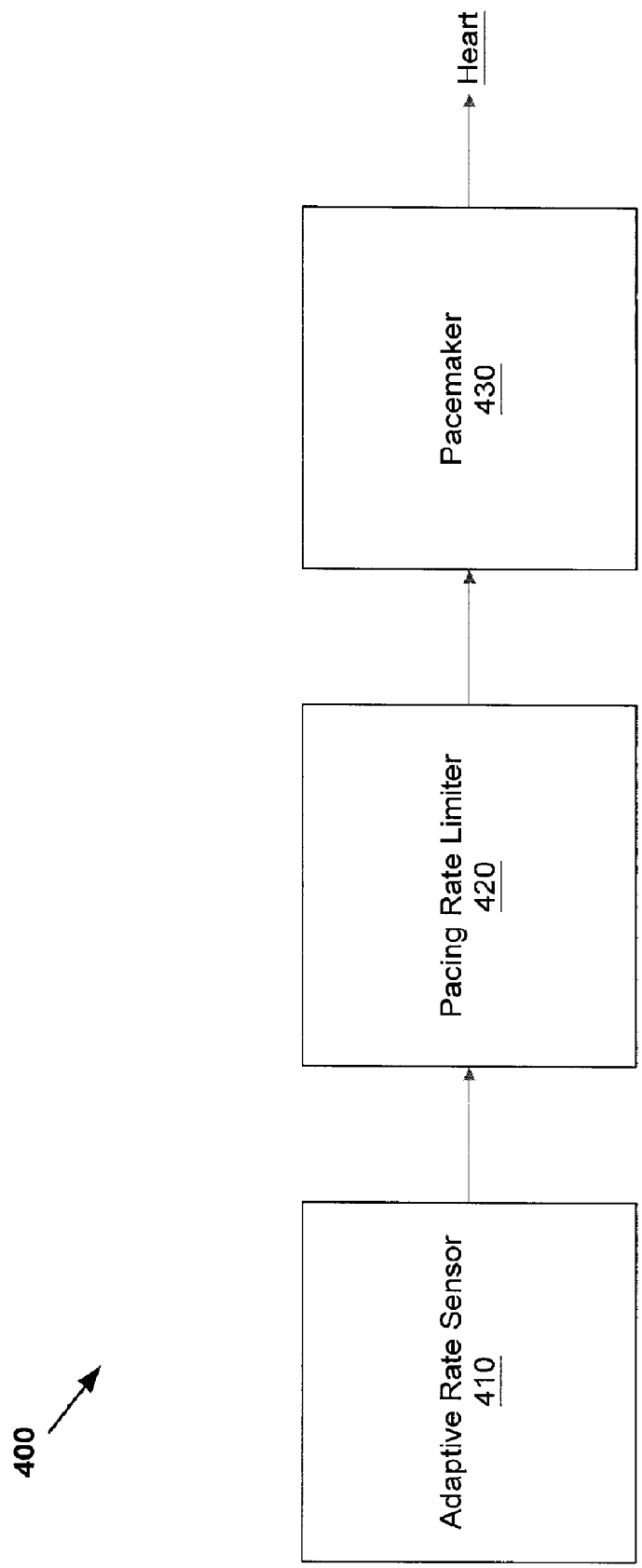
FIG. 4 illustrates a cardiac rhythm management system including a pacing rate limiter according to an embodiment of the present invention.

The methodology illustrated in FIG. 3 can be implemented in a pacing rate limiter as part of a CRM system. A CRM system 400 is illustrated in FIG. 4. Generally included are adaptive rate sensor 410, pacing rate limiter 420 according to a preferred embodiment of the invention, and a pacemaker 430. The adaptive rate sensor 410 may include any of the adaptive rate sensors as described above. Further, adaptive rate sensor 410 may also include an intrinsic atrial rate as measured by electrodes placed within the atria, as described above.

Adaptive rate sensor 410 is coupled to pacing rate limiter 420, and pacing rate limiter 420 is coupled to pacemaker 430. The adaptive rate sensor 410 may function to provide an adaptive-sensor indicated rate if adaptive rate sensor 410 is an adaptive rate sensor, or an intrinsic atrial rate. Pacing rate limiter 420 then selects a maximum pacing rate based on the minimum of an ERT rate calculated by the pacing rate limiter and the rate provided by 410. The pacing rate limiter 420 then communicates the maximum pacing rate to the pacemaker 430. Pacemaker 430 can then control the pacing stimulation frequency of electrical pulses communicated to the heart based on an escape interval as calculated from the maximum pacing rate.

It should be understood that the CRM system 400 as shown in FIG. 4 is by way of example only and that other configurations may be utilized without departing from the spirit of the invention. For example, it is possible that adaptive rate sensor 410, pacing rate limiter 420, and pacemaker 430 could all be implemented in a single unit or may be implemented as separate units. Further, adaptive rate sensor 410 could be coupled directly to pacemaker 430, and selection of the maximum pacing rate could be conducted by pacemaker 430 based on the rate provided by adaptive rate sensor 410 and the ERT rate from pacing rate limiter 420. Other configurations are also possible.

Figure 5:
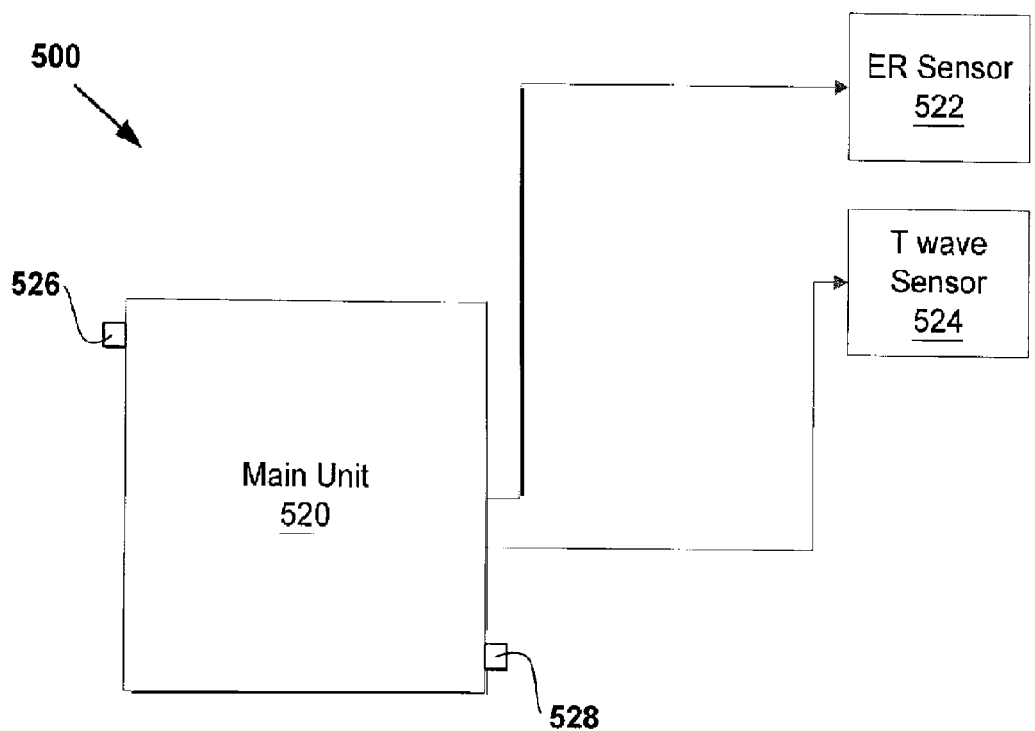
FIG. 5 illustrates in more detail a pacing rate limiter according to an embodiment of the present invention.

A pacing rate limiter 500 according to a preferred embodiment of the invention is shown in FIG. 5. The rate limiter 500 comprises a main unit 520 with an input port 526 and an output port 528. The main unit 520 is coupled to ER sensor 522 and T-wave sensor 524. Input port 526 is adapted to receive an adaptive-rate sensor indicated rate from an adaptive rate sensor, an intrinsic atrial rate, or other such pacing device. ER sensor 522 detects an evoked response and communicates detection of the evoked response to the main unit 520 of the pacing rate limiter 500. Similarly, T-wave sensor 530 is adapted to detect and communicate detection of the T-wave to main unit 520.

Output port 540 can be coupled to a pacemaker or other such CRM device for the heart. The pacing rate limiter 500 may calculate and communicate a maximum pacing rate to the pacemaker by way of output port 500. Once again, it should be understood that the embodiment shown in FIG. 5 is by way of example only, and that other configurations for pacing rate limiter 500 may be accomplished without departing from the invention. By way of example, the main unit 520 and sensors 522 and 524 may be implemented as a single unit or as separate units as shown. Further, the pacing rate limiter 500 may possibly be implemented as part of an adaptive rate sensor or as part of a CRM device.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A cardiac rhythm management system, comprising:
    a pacemaker configured to pace a heart at a paced heart rate; and
    a pacing rate limiter coupled to the pacemaker, the pacing rate limiter configured to couple to an ER sensor to detect a paced ventricular evoked response and to couple to a T-wave sensor to detect a T-wave;
    wherein the cardiac rhythm management system is configured to calculate an ERT interval based on the paced ventricular evoked response and the T-wave; and
    wherein the cardiac rhythm management system is configured to provide a maximum pacing rate based on the ERT interval.

2. The cardiac rhythm management system of claim 1, wherein the cardiac rhythm management system is configured to adjust the paced heart rate based on the maximum pacing rate.

3. The cardiac rhythm management system of claim 1, wherein the cardiac rhythm management system is configured to limit the paced heart rate based on the maximum pacing rate.

4. The cardiac rhythm management system of claim 1, further comprising an adaptive rate sensor module configured couple to an adaptive rate sensor and to measure an adaptive-rate sensor indicated rate,
    wherein the cardiac rhythm management system is configured to calculate an ERT rate based on the ERT interval, and wherein the cardiac rhythm management system is configured to compare the ERT rate to the adaptive-rate sensor indicated rate to provide a maximum pacing rate.

5. The cardiac rhythm management system of claim 4, wherein the cardiac rhythm management system is configured to select the maximum pacing rate as a minimum of the adaptive-rate sensor indicated rate and the ERT rate.

6. The cardiac rhythm management system of claim 4, wherein the adaptive rate sensor module includes the adaptive rate sensor.

7. The cardiac rhythm management system of claim 6, wherein the adaptive rate sensor includes at least one of a minute ventilation sensor, a QT interval sensor, or an electrode configured to provide an intrinsic atrial rate to the adaptive rate sensor module.

8. The cardiac rhythm management system of claim 6, wherein the adaptive rate sensor includes an accelerometer based activity sensor.

9. The cardiac rhythm management system of claim 6, wherein the adaptive rate sensor includes a transthoracic impedance based minute ventilation sensor.

10. The cardiac rhythm management system of claim 1, wherein the pacing rate limiter is configured to detect a segment of the T-wave selected from the group consisting of an onset of the T-wave, a peak of the T-wave, and a conclusion of the T-wave.

11. The cardiac rhythm management system of claim 1, wherein the cardiac rhythm management system is configured to average at least two ERT intervals to determine the ERT interval.

12. The cardiac management system of claim 1, wherein a single unit includes the pacemaker and the pacing rate limiter.

13. A cardiac rhythm management system for a heart, the system comprising:
    a pacemaker configured to pace a heart at a paced heart rate;
    a pacing rate limiter in communication with the pacemaker;
    an evoked response (ER) sensor in communication with the pacing rate limiter, wherein the pacing rate limiter and the ER sensor are configured to detect a paced ventricular evoked response;
    a T sensor in communication with the pacing rate limiter, wherein the pacing rate limiter and T sensor are configured to detect a T-wave; and an adaptive rate sensor in communication with at least one of the pacing rate limiter or the pacemaker, wherein the adaptive rate sensor is configured to provide an adaptive-rate sensor indicated rate, wherein the pacing rate limiter includes a main unit configured to calculate an ERT rate based on the detected paced ventricular evoked response and the detected T-wave, and wherein the pacing rate limiter is configured to communicate a minimum of the ERT rate and the adaptive-rate sensor indicated rate to the pacemaker as a maximum pacing rate.

14. The cardiac rhythm management system of claim 13, wherein the pacemaker is configured to adjust the paced heart rate based on the maximum pacing rate.

15. The cardiac rhythm management system of claim 13, wherein the pacemaker is configured to limit the paced heart rate based on the maximum pacing rate.

16. The cardiac rhythm management system of claim 13, wherein the adaptive rate sensor includes at least one of an activity sensor, a minute ventilation sensor, a QT interval sensor, or an intrinsic atrial rate.

17. The cardiac rhythm management system of claim 13, wherein the adaptive rate sensor includes an accelerometer based activity sensor.

18. The cardiac rhythm management system of claim 13, wherein the adaptive rate sensor includes an transthoracic impedance based minute ventilation sensor.

19. The cardiac rhythm management system of claim 13, wherein the ER sensor utilizes small coupling capacitor technology.

20. The cardiac rhythm management system of claim 13, wherein the pacing rate limiter is configured to detect the T-wave using one of an onset of the T-wave, a peak of the T-wave, or a conclusion of the T-wave.

* * * * *